United States Patent [19]

Current

[11] Patent Number: 4,628,113

[45] Date of Patent: Dec. 9, 1986

[54] ALCOHOL CARBONYLATION PROCESS USING A BIMETALLIC COBALT CATALYST

[75] Inventor: Steven P. Current, Novato, Calif.

[73] Assignee: Chevron Research Company, San Francisco, Calif.

[21] Appl. No.: 393,934

[22] Filed: Jun. 30, 1982

[51] Int. Cl.$^4$ .................. C07C 29/32; C07C 31/08; C07C 45/49; C07C 51/12; C07C 67/36
[52] U.S. Cl. .................. 560/232; 260/410.9 R; 260/413; 560/105; 560/114; 560/204; 562/406; 562/497; 562/519; 568/485; 568/486; 568/487; 568/594; 568/852; 568/902
[58] Field of Search ............... 560/206, 232, 265, 105, 560/114, 175, 204; 568/902, 903, 715, 594, 814, 852, 485–487, 861; 260/410.9 R, 413; 562/519, 406, 497

[56] References Cited

U.S. PATENT DOCUMENTS

| | | | |
|---|---|---|---|
| 2,593,440 | 4/1952 | Hagemeyer | 560/232 |
| 3,285,948 | 11/1966 | Butter | 568/902 |
| 3,387,043 | 6/1968 | Kuraishi et al. | 568/902 |
| 4,304,946 | 12/1981 | Isogai et al. | 568/902 |
| 4,431,835 | 2/1984 | Lafaye et al. | 560/105 |

FOREIGN PATENT DOCUMENTS 2089803A 6/1982 United Kingdom ............... 562/519

Primary Examiner—Vivian Garner
Attorney, Agent, or Firm—T. G. DeJonghe; C. J. Caroli

[57] ABSTRACT

A process for the preparation of carboxylic acids, alcohols, aldehydes or the secondary products thereof which comprises reacting an alcohol having from one to about twenty carbon atoms with hydrogen and carbon monoxide in the presence of a heterogeneous sulfided catalyst comprising cobalt in admixture with a co-catalyst selected from the elements of Groups V-B, VI-B and the Actinide series of the Periodic Table.

10 Claims, No Drawings

ALCOHOL CARBONYLATION PROCESS USING A BIMETALLIC COBALT CATALYST

BACKGROUND OF THE INVENTION

The present invention is concerned with a process for the preparation of oxygen-containing carbon compounds from alcohols and synthesis gas, wherein the compounds produced have at least one more carbon atom than the starting alcohol. More specifically, the present invention involves a process for the preparation of carboxylic acids, alcohols, aldehydes or the secondary products thereof by reaction of an alcohol with hydrogen and carbon monoxide in the presence of a heterogeneous bimetallic sulfided catalyst.

U.S. Pat. No. 2,623,906 discloses that at pressures above 1,000 atmospheres and in the presence of a cobalt catalyst, primary, secondary and tertiary alcohols react with synthesis gas to form glycol ethers and monohydric alcohols containing at least one more carbon atom per molecule than the original alcohol reactant.

U.S Pat. No. 3,285,948 discloses that an improved yield of ethanol from methanol can be obtained by conducting the synthesis gas homologation reaction in the presence of a cobalt catalyst which is promoted with iodine and a metal halide selected from ruthenium halide and osmium halide.

U.S. Pat. No. 4,111,837 discloses a process for producing ethanol which comprises reacting methanol with carbon monoxide and hydrogen in the presence of a catalyst consisting essentially of a methanol-soluble cobalt carbonyl and methanol-insoluble rhenium metal.

U.S. Pat. No. 4,304,946 discloses a process for producing ethanol from methanol, carbon monoxide and hydrogen which comprises conducting the reaction in the presence of a cobalt sulfide or a mixture of a cobalt sulfide and at least one of a nitrogen-containing compound and a phosphorus compound.

SUMMARY OF THE INVENTION

The present invention relates to a process for the preparation of carboxylic acids, alcohols, aldehydes or the secondary products thereof which comprises reacting an alcohol with hydrogen and carbon monoxide at a temperature in the range of about 150° C. to 350° C. and a pressure in the range of about 500 psig to 5,000 psig in the presence of a heterogeneous sulfided catalyst comprising cobalt in admixture with a co-catalyst selected from the elements of Groups V-B, VI-B and the Actinide series of the Periodic Table.

Among other factors, the present invention is based on my discovery that alcohols can be converted to useful oxygenated products having at least one more carbon atom than the starting alcohol in improved yield and selectivity by utilizing a heterogeneous bimetallic sulfided catalyst system.

An advantage of the present process lies in the fact that the heterogeneous catalyst employed is easier to separate from the reaction products than the homogeneous catalysts of the prior art.

In addition, it has been found that the present process does not require any soluble promoters or cocatalysts. This is particularly advantageous, since the absence of a halide promoter in the system obviates the need for expensive corrosion resistant equipment.

Oxygen-containing carbon compounds obtained with high selectivity in the process of the invention are carboxylic acids, alcohols, aldehydes or the secondary products which may be formed therefrom under the reaction conditions in a subsequent reaction, for example, esterification, condensation or dehydration.

DETAILED DESCRIPTION OF THE INVENTION

Illustrative of a typical batch procedure, the alcohol is charged to a high pressure reactor, and then there is introduced a heterogeneous bimetallic sulfided catalyst system comprising cobalt and an element of Groups V-B, VI-B or the Actinide series. The reactor is pressurized with a mixture containing carbon monoxide and hydrogen and heated for a suitable length of time to give the desired conversion. Liquid and gaseous products and reactants can be easily separated from the catalyst by filtration, distillation or other methods. Unreacted starting materials can be recycled. The products can be isolated by a number of known methods, including distillation. In some cases it may be advantageous to further process the products For example, methyl acetate can be easily hydrolyzed to acetic acid.

The process of the present invention can also be run in a continuous fashion. This is particularly advantageous as the catalyst is not soluble in the reaction medium. A number of reactor configurations are suitable including fixed and fluid beds, slurry beds and stirred tank reactors. As with a batch reaction, unreacted starting materials can be easily recycled and, if desired, the products can be further processed.

The alcohols suitable for use in the present invention may be primary, secondary, tertiary or benzylic alcohols having from one to about twenty carbon atoms. Diols and polyols may also be used. A preferred alcohol is methanol. If desired, the reactant alcohol may be diluted with an alcohol-miscible solvent such as dioxane, tetrahydrofuran, N-methylpyrroledinone, and the like. When methanol is used as the starting alcohol, reaction products typically formed include acetic acid, ethanol, acetaldehyde or methyl acetate.

The heterogeneous bimetallic sulfided catalyst system employed in the present process comprises a composite of sulfides of a cobalt component and a Group V-B, VI-B or Actinide component. Co-catalysts suitable for admixture with the cobalt component include tantalum, chromium, vanadium, thorium and tungsten. A particularly preferred catalyst system comprises cobalt and molybdenum. The catalyst system may optionally contain phosphorus or silicon.

In carrying out the reaction, it is usually desirable, although not essential, to place the catalyst on a support. Various supports suitable for use in the process are described in the prior art. Generally, the support should be a solid, inert material which is relatively insoluble in the solvent employed. Suitable supports include various treated or untreated organic and inorganic supports. Included among these are synthetic and naturally occurring polymers, alumina, silica, titania, silica-alumina, zeolites, glass, carbon, and the like. Particularly preferred supports are alumina and silica-alumina.

The metals may be added to the support using a number of methods known to the art such as by impregnation, co-precipitation, and the like. The method of loading the catalyst on the support will depend on the nature and composition of the support. Generally, the most convenient method of depositing the metals on the support is by adding a solution of metal salts to the support and subsequently converting them to an insoluble form.

An especially suitable catalyst precursor may be prepared by impregnating alumina with an aqueous or organic solution of the metal salts, either together or sequentially, followed by drying and calcining to give the metal oxides.

The catalyst may be converted to its active sulfide form by any of a number of conventional procedures. Treatment with hydrogen sulfide or other sulfur-containing compounds such as carbon disulfide, dimethyl disulfide or sulfur, in the presence of hydrogen or synthesis gas is effective. This treatment can be either prior to or concurrent with the alcohol carbonylation reaction.

In the process of the present invention alcohols are reacted with carbon monoxide and hydrogen (synthesis gas). Synthesis gas produced by the reaction of carbonaceous material with water is suitable. Mixtures of carbon dioxide and hydrogen, carbon monoxide and water, and the like, may also be employed. Whether introduced originally, or produced in situ under processing conditions, the reaction elements of carbon monoxide and hydrogen are required.

The relative molar quantities of carbon monoxide and hydrogen present during the reaction can vary in the range between about 10:1 and 1:10, and preferably in the range between about 3:1 and 1:3. An inert diluent gas such as nitrogen or helium may be included if desired.

The carbonylation reaction requires a relatively high pressure for optimum selectivity and yield of product. The pressure is maintained in the range between about 500 psig and 5,000 psig, and preferably in the range between about 800 psig and 2000 psig.

The reaction is conducted at a temperature in the range between about 150° C. and 350° C., and preferably in the range between about 190° C. and 290° C.

The time that the reactants are in contact with the catalyst will be dependent, among other factors, on the temperature, pressure, alcohol reactant, catalyst, reactor configuration and the desired level of conversion.

The solid catalyst can be easily separated from the generally liquid and gaseous reaction products and unreacted starting materials by, for example, filtration, centrifugation, settling out or distillation. The catalyst can be reused in a subsequent reaction. Unreacted starting materials can be separated from reaction products and are suitable for recycle in the process.

The products of the reaction, which can be isolated by a number of well-known methods such as distillation, are generally useful as solvents or chemical intermediates. In some cases it may be advantageous to further process the reaction products by well-known means to other useful products. For example, methyl acetate can be hydrolyzed to acetic acid, and ethanol and phenethyl alcohol can be dehydrated to ethylene and styrene, respectively.

The following examples are provided to illustrate the invention in accordance with the principles of this invention but are not to be construed as limiting the invention in any way except as indicated by the appended claims.

EXAMPLES

EXAMPLE 1

A cobalt-tantalum on alumina catalyst was prepared by impregnating 50.0 g of alumina with 32 ml of an ethyl acetate solution of 14.3 g tantalum pentachloride. The resulting solid was washed extensively with water and oven dried. The alumina was then further impregnated with 7.6 g of cobalt acetate tetrahydrate dissolved to give 32 ml of water solution. The catalyst was again oven dried, then calcined at 475° C. for 4 hours.

EXAMPLE 2

A 600 ml rocker bomb was charged with 75 ml methanol and 10.0 g of a cobalt-tantalum on alumina catalyst (described in Example 1) that had been previously treated with 10% hydrogen sulfide in hydrogen at 325° C. for 2 hours. The reactor was pressurized to 2,000 psi with a mixture of two parts hydrogen and one part carbon monoxide and heated with gentle rocking to 230° C. for a total of 12.5 hours. After cooling and venting the pressure, the liquid portion was analyzed by gas chromatography using 1,4-dioxane as an internal standard. Carbonylation products include methyl acetate (96.3 mmol), acetaldehyde dimethyl acetal (2.0 mmol), and ethanol (0.5 mmol). Other products include methyl ether, methyl formate (1.2 mmol) and water (221 mmol).

EXAMPLE 3

A 600 ml rocker bomb was charged with 100 ml methanol and 10.3 g of a 3% cobalt - 12% uranium on alumina catalyst (prepared by impregnating alumina with a water solution of cobalt acetate and uranyl nitrate, followed by calcination at 475° C.) that had been treated with 10% hydrogen sulfide in hydrogen at 325° C. for 2 hours. The reactor was pressurized to 2,000 psi with a mixture of two parts hydrogen and one part carbon monoxide, heated to 230° C., and gently rocked for 11.0 hours. After cooling and releasing the pressure, the liquid products were analyzed by gas chromatography using 1,4-dioxane as internal standard. Methyl acetate (41.0 mmol) is the major carbonylation product.

EXAMPLE 4

A 600 ml rocker bomb was charged with 100 ml methanol and 11.0 g of a catalyst comprising cobalt, molybdenum and phosphorus (approximately 3.2, 12.4 and 1.7 weight %) oxides on alumina that had been previously treated with 10% hydrogen sulfide in hydrogen at 325° C. for 2 hours. The reactor was pressurized to 2,000 psi with a mixture of two parts hydrogen and one part carbon monoxide, heated to 230° C., and gently rocked for 17.0 hours. After cooling and releasing the pressure, the liquid products were analyzed by gas chromatography using 1,4-dioxane as internal standard. The major carbonylation products are methyl acetate (63.6 mmol), ethanol (62.2 mmol), and acetaldehyde dimethyl acetal (10.1 mmol).

EXAMPLE 5

A 600 ml rocker bomb was charged with 100 ml methanol and 11.0 g of a 10% cobalt oxide on alumina catalyst (Harshaw Co-0501) that had been previously treated with 10% hydrogen sulfide in hydrogen at 325° C. for 2 hours. The reactor was pressurized to 2,000 psi with a mixture of two parts hydrogen and one part carbon monoxide, heated to 230° C., and gently rocked for 10 hours. After cooling and venting the pressure, the liquid portion was analyzed by gas chromatography using dioxane as an internal standard. The major carbonylation products are methyl acetate (18.1 mmol) and ethanol (10.6 mmol). Other products include methyl formate (3.0 mmol) and water.

EXAMPLE 6

A 300 ml stainless steel autoclave was charged with 75 ml methanol and 5.2 g of a catalyst comprising cobalt and tantalum on alumina (described in Example 1) that had been previously treated with 10% hydrogen sulfide in hydrogen at 325° C. for 1.5 hours. The reactor was pressurized with a mixture of one part hydrogen and two parts carbon monoxide to a pressure of 850 psi. The reactor was then heated to 240° C. and the pressure adjusted to 2,000 psi. After 6.0 hours, the reactor was cooled and the pressure released. The liquid products were analyzed by gas chromatography using 1,4-dioxane as internal standard. The major carbonylation product was methyl acetate (21.8 mmol).

EXAMPLE 7

A cobalt-molybdenum on alumina catalyst was prepared by impregnating 50 g of alumina with 34 ml of water solution containing 13.5 g of commercial phosphomolybdic acid hydrate and 7.8 g of cobalt acetate tetrahydrate. The catalyst was dried for 16 hours at 125° C. and then calcined at 475° C. for 4 hours.

EXAMPLE 8

A 300 ml stainless steel autoclave was charged with 75 ml methanol and 5.26 g of cobalt-molybdenum on alumina catalyst (described in Example 7) that had been previously treated with 10% hydrogen sulfide in hydrogen at 325° C. for 2.5 hours. The reactor was further charged with 900 psi of a mixture of two parts carbon monoxide and one part hydrogen and heated to 235°–240° C. The pressure was adjusted to 2,000 psi. After heating for 6 hours, the reactor was cooled and the pressure vented. Analysis of the liquid portion by gas chromatography using dioxane as an internal standard indicated that the major carbonylation products are methyl acetate (9.2 mmol) and ethanol 7.54 mmol).

EXAMPLE 9

An unsupported cobalt-tungsten catalyst was prepared by dissolving 21.1 g cobalt (II) acetate tetrahydrate and 30.0 g silicotungstic acid (app. $H_4SiW_{12}O_{40}.24H_2O$) in approximately 10 ml of hot water, slowly evaporating to dryness, and finally calcining at 450° C. for 3 hours.

EXAMPLE 10

A 300 ml stainless steel autoclave was charged with 75 ml methanol and 5.1 g of the cobalt-tungsten catalyst described in Example 9 that had previously been treated with 10% hydrogen sulfide in hydrogen at 325° C. The autoclave was pressurized to 900 psi with a mixture of two parts hydrogen and one part carbon monoxide and heated to 240° C. The pressure was adjusted to 2,000 psi. After heating for 8 hours, the reactor was cooled, pressure vented, and liquid products analyzed by gas chromatography using 1,4-dioxane as an internal standard. The major carbonylation products are methyl acetate (10.0 mmol), methyl formate (4.4 mmol) and ethanol 0.7 mmol).

What is claimed is:

1. A process for the preparation of carboxylic acids, alcohols, aldehydes or carboxylic acid esters which comprises reacting a primary, secondary, or tertiary alcohol having from one to about twenty carbon atoms with hydrogen and carbon monoxide at a temperature in the range of about 150° C. to 350° C. and a pressure in the range of about 500 psig to 5,000 psig in the presence of a heterogeneous sulfided catalyst comprising a composite of sulfides of a cobalt component and a Group V-B, VI-B or Actinide element component and in the absense of a halide promoter, wherein the reaction products formed have at least one more carbon atom than the starting alcohol.

2. The process according to claim 1, wherein the sulfided catalyst contains cobalt and molybdenum.

3. The process according to claim 1, wherein the sulfided catalyst further comprises phosphorus or silicon.

4. The process according to claim 1, wherein the sulfided catalyst is present on a support.

5. The process according to claim 4, wherein the support is alumina or silica-alumina.

6. A process for the preparation of acetic acid, ethanol, acetaldehyde, methyl acetate, methyl ether or acetaldehyde dimethyl acetal which comprises reacting methanol with hydrogen and carbon monoxide at a temperature in the range of about 150° C. to 350° C. and a pressure in the range of about 500 psig to 5,000 psig in the presence of a heterogeneous sulfided catalyst comprising a composite of sulfides of a cobalt component and a Group V-B, VI-B or Actinide element component and in the absence of a halide promoter.

7. The process according to claim 6, wherein the sulfided catalyst contains cobalt and molybdenum.

8. The process according to claim 6, wherein the sulfided catalyst further comprises phosphorus or silicon.

9. The process according to claim 6, wherein the sulfided catalyst is present on a support.

10. The process according to claim 9, wherein the support is alumina or silica-alumina.

* * * * *